(12) United States Patent
Kim et al.

(10) Patent No.: US 7,087,246 B2
(45) Date of Patent: Aug. 8, 2006

(54) CONTROLLED RELEASE PREPARATION OF INSULIN AND ITS METHOD

(75) Inventors: Chan-Hwa Kim, Seoul (KR);
Jai-Hyun Kwon, Seoul (KR);
Sung-Hee Choi, Seoul (KR)

(73) Assignee: Mi Tech Company Limited, Seoul (KR)

( * ) Notice: Subject to any disclaimer, the term of this patent is extended or adjusted under 35 U.S.C. 154(b) by 498 days.

(21) Appl. No.: 10/312,044

(22) PCT Filed: Jun. 25, 2001

(86) PCT No.: PCT/KR01/01085

§ 371 (c)(1),
(2), (4) Date: Dec. 23, 2002

(87) PCT Pub. No.: WO02/00207

PCT Pub. Date: Jan. 3, 2002

(65) Prior Publication Data

US 2003/0125237 A1    Jul. 3, 2003

(30) Foreign Application Priority Data

Jun. 27, 2000  (KR) ............................... 2000/35760
Dec. 29, 2000  (KR) ............................... 2000/85698

(51) Int. Cl.
*A61K 9/50*    (2006.01)
*A61K 9/14*    (2006.01)
*A61K 9/16*    (2006.01)
*A01N 25/08*   (2006.01)
*A01N 25/26*   (2006.01)

(52) U.S. Cl. ...................... 424/499; 424/409; 424/418; 424/489; 424/497

(58) Field of Classification Search ................ 424/408, 424/409, 418, 489, 497, 499; 523/105
See application file for complete search history.

(56) References Cited

FOREIGN PATENT DOCUMENTS

| JP | 9-315997 | 12/1997 |
|---|---|---|
| WO | WO 99/55310 | 11/1999 |

*Primary Examiner*—Shin-Lin Chen
(74) *Attorney, Agent, or Firm*—Volentine Francos & Whitt, PLLC

(57) ABSTRACT

A controlled release preparation of insulin and its method are provided. The controlled release preparation of insulin contains microparticles obtained by microencapsulation of uniform microcystals of insulin using biodegradable polymeric materials. Since the denaturation of insulin that may occur during microencapsulation is reduced, the stability of the preparation can be increased. Also, the ratio of insulin to a polymer carrier is increased, which is suitable for pulmonary delivery. Further, the controlled release preparation of insulin can continuously exhibit pharmaceutical efficacy in vivo in a stable manner for an extended period of time.

12 Claims, 12 Drawing Sheets

25μm

50μm solution / PLGA (■)
crystal / PLGA (□)

solution / PLGA (■)
crystal / PLGA (□)

insulin crystal (●)

freeze-dried crystal/PLGA(○)

non-freeze-dried crystal/PLGA(▼)

pH3(●)
pH6(○)
pH7.4(▼)

PBS(●)

insulin solution (2 IU/kg)(○)

insulin crystal (5 IU/kg)(▼)

crystal/PLGA (20 IU/kg)(▽)

CONTROLLED RELEASE PREPARATION OF INSULIN AND ITS METHOD

TECHNICAL FIELD

The present invention relates to a controlled release preparation of insulin and its method, and more particularly, to a controlled release preparation of insulin containing microparticles obtained by microencapsulation of uniform microcrystals of insulin using biodegradable polymeric materials, and its method.

BACKGROUND ART

In general, a drug is processed into a formulation by which pharmacological efficacy can be optimally exhibited, and is then administered into a living body through various routes. The administered drug is released from the formulation and exhibits various pharmaceutical effects in vivo while undergoing absorption, distribution, metabolism and excretion. In order for the drug to safely and effectively exhibit its pharmaceutical efficacy in vivo and to be selectively active on an intended site of the body, it is necessary to control the behavior of drug in vivo. A drug delivery system (DDS) is a formulation designed to effectively deliver an appropriately necessary amount of drug by maximizing the efficacy of drug while suppressing side effects of drug.

Although DDS has not yet been completely defined, it has been used to embrace in a broad sense the meaning of a wide range of formation designs controlling the behavior of drugs in vivo, inclusive of a targeting system and a chemical delivery system, and to embrace in a narrow sense the meaning of a controlled release system.

Controlled drug release methods have rapidly developed in pharmaceutical fields since the 1970s. A micromolecular controlled release system has been typically applied in medical fields, and it has been in particular utilized in delivering pharmaceutical products to a specific site of the human body.

A controlled release system exists in various forms including capsules for oral administration, matrices, microcapsules for oral administration and injection, microspheres, microparticles, nanoparticles, liposomes and implants (J. Kost, 1995).

Microencapsulation

Microencapsulation is the most important technique in controlled release preparation. In this field, as nano-technology is combined with the development of drug delivery systems in the pharmaceutical fields, the of microparticles has rapidly developed.

For example, experiments in which pseudophedrine HCl, which is a soluble pharmaceutic product, is entrapped in polymeric microspheres using oil-in-water (O/W) dispersion or co-solvent methods, water-in-oil-in-water (W/O/W) multiple emulsion method or an emulsion-solvent evaporation method, have demonstrated that an appropriate amount of drug can be loaded (R. Bodmeier et al., 1991). A microcapsule refers to a spherical particle having solid or liquid drug positioned at a center nucleus, and a microsphere refers to multiple nuclei in which solid or liquid drug is dispersed in a polymeric material. A microparticle is used to embrace microcapsules and microspheres, and refers to a microparticular drug carrier using microparticles such as a polymeric matrix or lipid as a drug carrier. Unless specified otherwise throughout the specification, these terms are used to those described above.

Microparticles can be produced to have various diameters ranging from 0.1 μm to several hundreds of micrometers (μm). Among those microparticles, ones having a diameter of 1 μm or less are referred to as nanospheres (or nanoparticles). Most microspheres generally preserved in a solid phase to be suspended during use have been traditionally used as radiation diagnosis reagents, and much attention has been recently paid thereto as a drug carrier.

Drug carrier

Physical supports (carriers) for use in a controlled release system include various types of synthetic and natural rubber. Among them, biodegradable polymers are albumin, gelatine, collagen, fibrinogen, polylactides (PLA), polyglycolides (PGA), poly β-hydroxy butyric acids (PHB), polycaprolactone, polyanhydrides, polyorthoesters, poly(lactic-co-glycolic) acid (PLGA), which is a copolymer of these materials, and the like. These polymers were developed in the 1960s as surgical suture threads, and various kinds of research into the polymers as systems of sustained release preparation such as steroids, anti-malaria agents, narcotic inhibitors or carcinostatis substances have been made since the 1970s. After Tice et al. disclosed that sustained release could be achieved by producing water-soluble compounds, e.g., antibiotics and luteinizing hormone-releasing hormone (LHRH) analogues, from microsphere preparations, much more attention has been being paid to the above-described biodegradable polymers (Tice, T. R. (1984) *Pharm. Tech.* 8, 26–36).

PLGA

In order to achieve microencapsulation of peptides with copolymers, the following requirements must be met:

1) The peptides must be formed of biodegradable polymers;
2) The denaturation of peptides must not occur during the process; and
3) Encapsulation efficiency must be sufficiently high.

Currently, main research into microencapsulation of peptides and proteins is a water-in-oil-in-water (W/O/W) solvent evaporation technique using poly-(lactic acid) (PLA) or poly(lactic-co-glycolic) acid (PLGA) which is a PLA and poly-glycolic acid (PGA) copolymer.

The PLGA and PLA are polymers that are fully supported by toxicological and clinical data and are nontoxic, biocompatible, biodegradable polymers that are authorized by the FDA to be used for the human body. Glycolic acid and lactic acid which are denatured from these materials are removed through internal metabolism. Since the rate of hydrolysis of those polymers depends upon temperature, the presence of a catalyst and a definite change in pH, a change in the rate of denaturation depending upon the position in the body is not observed. This satisfies requirements suitable for use in drug delivery formulation. The rate of denaturation is determined by the molecular weight and crystallinity of a polymer and the lactide:glycolide ratio of the PLGA. Since the lactic acid has asymmetric carbon atoms, it has two optical isomers. Thus, the polymers consist of L, D- and D, L-lactic acid. The L, D-polymer is in a crystalline form, the D, L-polymer is in an amorphous form and these polymers are denatured rapidly (Patrick Convreur, Maria Jose, Blanco-Prieto, Francis Puisienx, Bernard Reques, Elias Fattal, Multiple emulsion technology for the design of microspheres containing peptides and oligopeptide, *Advanced Drug Delivery Review* 28 (1997) 85–96).

The PLGA is used in microencapsulation of water-soluble and insoluble pharmaceutical products. In the case where microspheres were produced using bovine serum albumin (BSA) as a model protein by an oil-in-oil (O/O), oil-in-water (O/W) or water-in-oil-in-water (W/O/W) emulsion method, it turned out that 50 to 70% of the overall proteins injected into a formulation medium was contained in the microspheres and the particle sizes thereof were 500 μm, 25 to 100 μm and 10 to 20 μm, respectively. The release types of BSA were different according to the method. In the case of microspheres vacuum dried after being produced by the W/O/W emulsion method, the release amount thereof was large. In the case of microspheres containing carbopol-R 951 and produced by the O/W method, the 5 initial burst amounts were large. The release lasting periods were 54 days, 36 days and 34 days, respectively.

Also, in the case of microspheres produced from PLGA by a double emulsion method, it was reported that the microspheres were produced in a size suitable for pulmonary delivery. In the case of microspheres produced using Ciliary neurotrophic fact (CNTF) and PLGA in a mixture ratio of 30:70 (D. Maysinger, et al. 1996), it was reported through phase analysis that the average particle size of the microspheres was 1.76±0.0186 μm.

Insulin

Insulin is one of targets of controlled release preparation that is being researched most vigorously. Currently, the most typically used insulin is in the form of injection and pump. 40, 80 and 100 IU/ml of Zn-insulin suspensions or neutral solutions, which typically have immediate effects, are in widespread use, and 100 IU/ml is generally preferred in use. Insulin tends to exhibit fast efficacy in a solution state rather than in a crystal state, while having a short time in a protracted action. Thus, patients use insulin mostly in the form of injections before meals or before sleeping. According to activity, immediately active insulin and protractedly active insulin are separately administered. Such existing insulin preparations are an inconvenience in a patient's daily life due to the necessity of frequent administrations of insulin. In the case of missing an administration, a sharp decrease in the serum glucose concentration or a significant risk of hypoglycemia may occur.

It is known that insulin crystals have longer pharmaceutical efficacy than insulin solutions and are active for about 36 hours when they are administered. This is because insulin crystals slowly dissolve insulin in the body, which can be advantageously used in protracting the activity of insulin within blood, in a manner similar to that in which insulin is generated and secreted from the pancreas of the human body. On the basis of this fact, in 1956, Schlichtkrull attempted to generate insulin crystals small enough to be used for treatment of diabetes. Thereafter, in the pharmacy field, continuous research has been conducted into crystallization methods for making microcrystals of insulin or insulin derivatives so as to be slowly dissolved in the body. Many reports of insulin crystallization methods have been hitherto made, and most reports have utilized a change in the pH of insulin solution (U.S. Pat. Nos. 3,719,655 and 4,959,351). However, these conventional crystallization methods present a problem in that fine insulin crystals of 10 μm or less, which are suitable for administration through the lung, cannot be obtained at high yield.

Various researches are being conducted into controlled release preparation of insulin which is capable of reducing the concentration of serum glucose continuously for a long time after administration in vivo, and among them, several insulin controlled release preparations have shown significant developments. Most insulin delivery systems currently being researched are based on the reaction between glucose-oxidase tied up into a polymer in a drug delivery system (DDS) and glucose present in blood. If the reaction between glucose and glucos-oxidase results in a decrease in the pH in the microenvironment of the DDS, a polymer system is swollen so that the amount of released insulin increases. The polymer system used herein includes N,N-dimethylaminoehtyl methacryalte and poly-acrylamide.

Alternatively, in order to prevent insulin for oral administration from being denatured in the digestive system, nanospheres may be produced. According to this method, protein denaturation is prevented by a polymer matrix before being absorbed through intestinal M cells and the polymer matrix of a small size allows permeation through a membrane barrier. This method is advantageous in view of the convenience in administration. However, the delivery effect of this method is only 11% the effect of abdominal delivery (Gerardo P. Carino, Jules S. Jacob, Edith Mathiowitz, Nanosphere based oral insulin delivery, *Journal of Controlled Release* 65 (2000) 261–269).

Pulmonary delivery is one of the active researches that are currently being conducted. The pulmonary delivery provides a relatively wide surface area as large as a wide tennis court, e.g., 100 m$^2$, compared to nasal delivery, and allows for fast absorption through a vast number of blood vessels present over thin epithelial cell walls. According to the results of clinical trials conducted by several companies, announced in a conference of the America Diabetes Association, the same effect as injected insulin could be obtained. It is known that a clinical trial phase III in which approximately 1,000 patients are the subjects of the clinical experimentation is under way. The development of a delivery system of protein pharmaceutical products using pulmonary delivery is expected to propose ways of easy and convenient administration of protein pharmaceutical products that have been conventionally supplied only through injection. The present invention provides an effective controlled release preparation of insulin in the context of pulmonary delivery of insulin.

Stability of protein pharmaceutical products

In the case of small peptides, even if decomposition thereof scarcely occurs, the stability thereof is an essential issue. In the course of producing microparticles, proteins or peptides are applied to excess stress. Thus, the microencapsulation process of protein pharmaceutical products must be free from excessive heat and shear stress, a sharp change in pH, organic solvent and excessive freezing and drying. The microencapsulated proteins may be hydrated even during storage and the proteins are prone to denaturation and aggregation under these circumstances. When the polymer begins to be decomposed after being administered, a highly concentrated acidic microenvironment is created inside and around the polymer due to decomposed acidic monomer. Under these circumstances, the proteins are prone to aggregation, hydrolysis and chemical change. Finally, the proteins may cause reversible or irreversible partition together with the polymer, thereby affecting a drug delivery rate, finally leading to denaturation, aggregation and inactivation of proteins.

Among peptides for therapeutic purposes, insulin becomes a target of a nuclease and is prone to chemical, physical denaturation in a solution or suspension (J. Brange, L. Andersen, E. D. Laursen, G. Meyn, E. Rasmussen, Toward understanding insulin fibrillation, *J. Pharm. Sci.* 86 (1997) 517–525).

Deamidated products may be generated in a liquid phase solution due to chemical decomposition of insulin, e.g., desamido A21 in acidic media or desamido B3 in a neutral solution. Otherwise, insulin dimers having a covalent bond may be formed by transamidation (R. T. Darrington, B. D.

Anderson, Evidence for a common intermediate in insulin deamidation and covalent dimer formation; effects of pH and aniline trapping in dilute acidic solutions, *J. Pharm. Sci.* 84 (1995) 274–282).

Like other globular proteins, insulin has a tertiary structure in which the hydrophobic surface thereof is concealed inside through folding or assembly of various molecules. Otherwise, a change of its native conformation may be affected for various reasons. Specifically, heat, physical force and exposure to hydrophobic surface cause a structural change of proteins, thereby resulting in aggregation of proteins and producing insoluble precipitates (B. V. Fisher, P. B. Porter, Stability of bovine insulin, *J. Pharm. Pharmacol.* 33 (1981) 203–206).

The denaturation of protein pharmaceutical products causes immunogenicity or antigenicity, accompanied by generation of antibodies, impeding the activation of injected proteins and affecting the action of an identical protein spontaneously generated in the human body, which is very hazardous.

Therefore, consideration must be taken into the stability of pharmaceutical products in view of formulation as well as . The present invention relates to a microencapsulation method while attaining stability of insulin contained in formulations.

Disclosure of the Invention

Formulation and drug delivery are very important factors in developing protein pharmaceutical products using gene recombinant technology. In particular, since biological and pharmaceutical products have a large molecular weight and a tertiary structure, on which the activity and physical property are greatly dependent, they are easily prone to denaturation, compared to general chemical synthetic drugs. As a result, formulation becomes an important issue in view of structural stability.

Since insulin is easily denatured during microencapsulation, it is liable to generate deamindated products, and approximately 50% of a loss in the overall proteins occurs. Also, the initial burst occurring due to partition on the surface of the protein while drying microparticles, may cause hypoglycemic effects.

Therefore, it is a first object of the present invention to provide a controlled release preparation of insulin, which can minimize protein denaturation of insulin and can increase stability in the course of microencapsulation, and its method thereof.

To this end, the present invention provides a controlled release preparation of insulin, by which microparticles of insulin are microencapsulated using a polymer carrier. The controlled release preparation according to the present invention can be made in various forms suitable for pulmonary inhaled administration, injection, oral administration, transdermal suction and so on. In particular, the size of the microparticles is 10 μm or less, preferably 5 μm or less, so as to be suitably used for pulmonary delivery. The insulin controlled release preparation according to the present invention is a sustained release preparation which can reduce the number of administrations of insulin owing to continuous exhibition of pharmaceutical efficacy. Also, according to the present invention, the amount of initial burst of insulin can be controlled to prevent a sharp decrease in the serum glucose concentration.

It is another object of the present invention to provide increased encapsulation efficiency and optimization of insulin.

Biodegradable polymers used for microencapsulation differ in decomposition rate according to physical properties and compositions thereof, and a considerable time is required for complete decomposition. In the case of PLGA whose safety relative the human body has already been verified, it is generally known that approximately 50 days to approximately 100 days are required for decomposition of the PLGA even if the decomposition rate thereof may differ according to the composition. Thus, if a microencapsulated preparation using a biodegradable polymer as a carrier is continuously administered, polymer accumulation in a living body may occur. Therefore, it is an object of formulation technology to entrap a larger amount of drug using the same amount of the polymer carrier in microencapsulation.

In the case of microencapsulation of a drug in a liquid state, the concentration of the drug that can be entrapped in microparticles is determined by the solubility of the drug. If the solubility of the drug is low, only a small amount of the drug is entrapped. In this case, in order to deliver an appropriate amount of the drug, it is necessary to administer a much greater volume of microparticles into a living body.

This problem becomes serious in the case of pulmonary delivery. In general, a substance delivered through the lung is subjected to internal absorption. A non-absorptive substance is removed by a clearance process using macrophages. The clearance process takes more time in the blastosphere than in the airway where the delivered substance is removed within 24 hours (Camner, P. 1994). Also, it was reported in a paper that the clearance process is carried out more slowly when more substances exist in the lung.

Therefore, in particular, when a drug is administered through the lung, it is necessary to reduce an amount of polymeric substance to be administered into a body by increasing the ratio of the drug to the polymer carrier. In the present invention, there is provided a controlled release preparation of insulin, by which the content of insulin contained in microparticles can be adjusted as needed by producing microparticles using uniform microparticles of insulin.

It is a still another object of the present invention to provide a method of preserving microparticles of insulin in a liquid phase in order to solve the inconvenience of use of microencapsulated insulin, that is, the microencapsulated insulin should be again dispersed in a solution.

Generally, microparticles are freeze-dried for storage and dispersed prior to use. However, in the case of protein pharmaceutical products, denaturation may occur in the course of freeze-drying. Also, initial burst may occur due to surface partition of the microparticles of the drug, which is caused in the course of drying. Thus, in order to facilitate drug administration and to prevent initial burst, the present invention provides a method of preserving a microparticle preparation of insulin in a solution using an isoelectric point without freeze-drying the microparticle preparation of insulin.

Alternatively, the present invention provides a controlled release preparation of insulin and its method, by which immediate and protracted effects can be simultaneously attained at a single administration by including an immediately active portion of insulin in the preparation together with microparticles of insulin crystals.

The other objects and advantages of the present invention will be described below and will be apparent by embodiments of the present invention.

BRIEF DESCRIPTION OF THE DRAWINGS

FIG. 1 shows photographs taken by an inverted microscope, illustrating microencapsulation of insulin crystals and an insulin solution using a double emulsion method, in which FIG. 1A shows an microencapsulated insulin solution (×400), FIG. 1B shows an microencapsulated insulin microparticles (×400), FIG. 1C shows an microencapsulated insulin solution (×200) and FIG. 1D shows an microencapsulated insulin microparticles (×200);

FIG. 2 shows photographs taken by an inverted microscope, illustrating microencapsulation insulin crystals and an insulin solution using a double emulsion method, in which FIG. 2A shows an microencapsulated insulin solution (×1300, scale bar: 30 µm), FIG. 2B shows the surface of an microencapsulated insulin solution (×5000, scale bar: 6 µm), FIG. 2C shows the cross-section of an microencapsulated insulin solution (×9000, scale bar: 6 µm), FIG. 2D shows microencapsulated insulin crystals (×1300, scale bar: 30 µm), FIG. 2E shows the surface of microencapsulated insulin crystals (×4700, scale bar: 6 µm), and FIG. 2F shows the cross-section of microencapsulated insulin crystals (×9000, scale bar: 6 µm);

FIGS. 5A through 5D are graphs showing the observation results of deamidated products with RP-HPLC after releasing solution/PLGA and crystal/PLGA for 7 days, in which FIG. 5A is for the case of non-freeze-dried solution/PLGA, FIG. 5B is for the case of non-freeze-dried crysta/PLGA, FIG. 5C is for the case of freeze-dried solution/PLGA and FIG. 5D is for the case of freeze-dried crystal/PLGA;

BEST MODE FOR CARRYING OUT THE INVENTION

Figure 1:
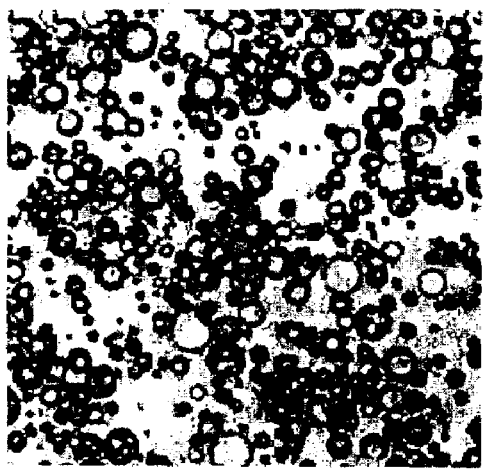
Figure 1:
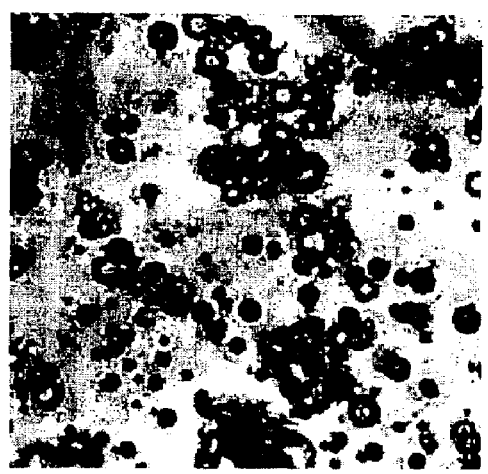
Figure 1:
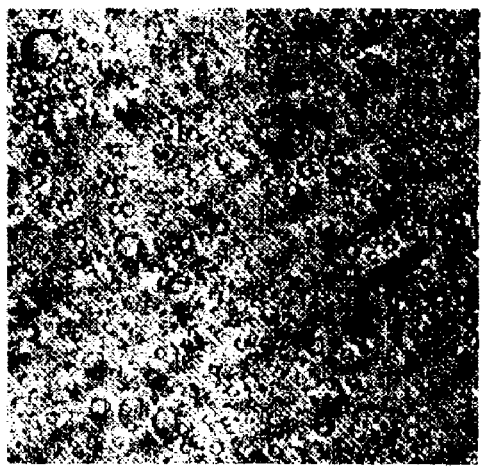
Figure 1:
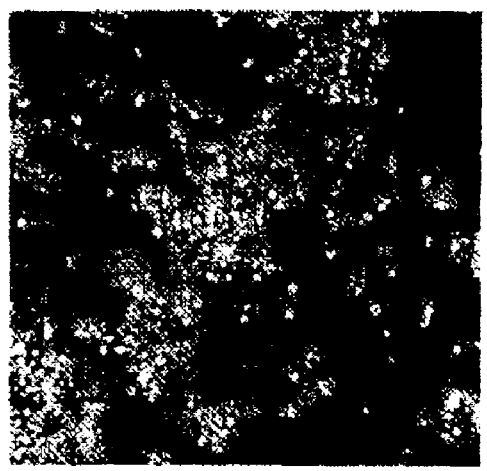

Microencapsulation of insulin crystals according to the present invention will now be described in detail.

In order to produce microparticles using uniform microcrystals of insulin, it is necessary to find out a crystallization method of insulin, by which insulin microcrystals can be produced at high yield. In the prior application, the inventors of the present invention proposed a method of producing insulin microcrystals of 10 µm or less, preferably 5 µm or less, at high yield, by forming insulin seeds that can act as nuclei of crystals by adjusting the solubility of insulin in the solution, and then reducing the solubility of insulin in the solution for crystallization (Korean Patent Application No. 99-14957). In the present invention, the present inventors achieved microencapsulation of insulin microcrystals by employing the proposed crystallization method.

A method of attaining uniform insulin microcrystals will now be described. While varying the pH of an acidic insulin solution, which is at an isoelectric point or below up to approximately 9 to approximately 10.5, insulin seeds in the insulin solution are formed and then the solubility of insulin in the solution is lowered, consequently insulin microcrystals of 10 µm or less, preferably 5 µm or less are formed.

In general, microparticles are produced by emulsifying a matrix polymer with a drug and denaturation by heating; chemical crosslinkage using formalin; or hardening using radiation polymerization and in-water drying. The microparticle size, which is an important factor to determine the internal behavior of the drug, can be adjusted by selecting appropriate preparation conditions.

Peptides are hydrophilic when N- and C-terminus thereof are not blocked by ring formation, amidation or esterification. Thus, peptides and proteins are difficult to microencapsulate in a polymeric matrix preparation consisting of hydrophobic polymers due to hydrophilicity. Because of these properties, methods of producing microparticles using a W/W/W solvent evaporation method have been developed.

A multiple emulsion solvent evaporation method involves an inner water phase (IWP) which is drug dissolved in distilled water or a buffered solution and an organic solvent (OS) which is a polymer dissolved in a water immiscible, highly volatile solvent. The IWP is emulsified in the OS to make a primary emulsion (W/O) and then stirred while pouring the same into an outer water phase (OWP) containing an emulsifier to make a secondary emulsion (W/O/W). The resultant multiple emulsion is continuously stirred to evaporate the OS, causing precipitation of the polymer, thereby forming drug-loaded microparticles.

The presence of an emulsifier in OWP plays an important role in the formation of rectangular microparticles. The emulsifier functions to prevent coagulation of microparticles during removal of OS. Poly(vinylalchol) (PVA) is generally used as the emulsifier and usable emulsifiers include polyvinylpirrolidone, alginates, methylcellulose, gelatine and the like.

Removal of OS is performed under normal pressure or reduced pressure. Perfect removal of OS can be performed by the following three processes.

1) Interrupted process: While evaporation is performed at room temperature, partially hardened microparticles are transferred to a low-concentration emulsifier solution or an emulsifier-free solution for continuous evaporation;

2) Continuous process: Continuous stirring is performed at room temperature until OS is completely removed; and 3) Rotary evaporation: OS is removed at approximately 30° C. using a rotary evaporator.

The hardened microcapsules produced after removing OS are filtered by filtration or centrifugation, washed several times for removing the emulsifier and then vacuum-dried or freeze-dried.

In the present invention, microencapasulation is preferably performed by a double emulsion method, and biodegradable polymers are used. Examples of biodegradable polymers include albumin, gelatin, collagen, fibrinogen; hydroxy acids such as polylactides (PLA) and polyglycolides (PGA); poly(lactide-co-glycolide)s (PLGA), polyethylene glycol (PEG), poly β-hydroxy butyric acid (PHB), polycaprolactone, polyanhydrides, polyortho esters, polyurethanes, poly(butyric acid)s, poly(valeric acid)s, poly(lactide-co-caprolactone) and derivatives thereof, and copolymers and blends thereof. The term "derivatives" as used herein comprises polymers having substitution of chemical groups, e.g., alkyl or alkylene, addition, hydroxylation, oxidation and other modifications made by one skilled in the art in a conventional manner. In general, biodegradable polymeric materials are degraded in vivo by both non-enzymatic and enzymatic hydrolyses and surface or bulk erosion. A usable polymeric material is preferably poly(lactide-co-glycolide)s (PLGA).

The microencapsulation according to the present invention using a double emulsification solvent evaporation procedure will now be described in detail.

First, the insulin microcrystals are obtained in the above described manner and suspended in a solution of the pH from 4.5 to 6.5, that is, at an isoelectric precipitation zone of insulin, to then be used.

Here, usable suspensions include a chitosan solution produced by adding a base to a 1% chitosan solution produced from a 1% acetate solution and adjusting the pH at 4.5 to 6.5, that is, at an isoelectric precipitation zone, at which insulin crystals are not dissolved. Here, a phosphate buffered saline (PBS) may be used instead of chitosan. Further, a supernatant solution of insulin crystals which was obtained in a crystallization process can also be used.

The insulin suspension prepared in the above described method is added to a polymeric solution, e.g., a PLGA/DCM solution, to make a primary emulsion. The primary emulsion is added slowly to an emulsifier, e.g., a 1% PVA solution, to make a secondary emulsion, and then stirred to be coagulated. Then, particles are recovered by centrifugation, washed with distilled water three times and freeze-dried, thereby obtaining microparticles according to the present invention.

General emulsifiers such as polyvinylalchol (PVA), polyvinylpirrolidone, alginates, methylcellulose, gelatine and the like can be used as the emulsifier.

The microparticles according to the present invention prepared in the above-described process have a small, uniform particle size distribution of 10 μm or less, preferably 0.1 μm or greater, in volume average diameter. In particular, in the case of formulations for pulmonary administration, the microparticles preferably have a diameter of 5 μm or less. The particle size is not affected by an amount of insulin crystals contained in the microparticles.

In the following examples, the microparticles according to the present invention prepared by microencapsulation of insulin crystals and insulin solution were compared. The used insulin solution was prepared by dissolving insulin in an acetic solution.

The result of various comparative examples showed that microcapsules in which a drug is positioned at the central nucleus in the case of microencapsulating insulin crystals, to be referred to as "crystal/PLGA", are formed, and microspheres in which drug is dispersed in a polymeric material in the case of microencapsulating a liquid-phase insulin solution, to be referred to as "solution/PLGA", are formed (see FIG. 1). Based on the formulation structure, the crystal/PLGA of the present invention showed a smaller, more uniform particle size distribution than the solution/PLGA (see FIGS. 3 and 4).

Figure 6:
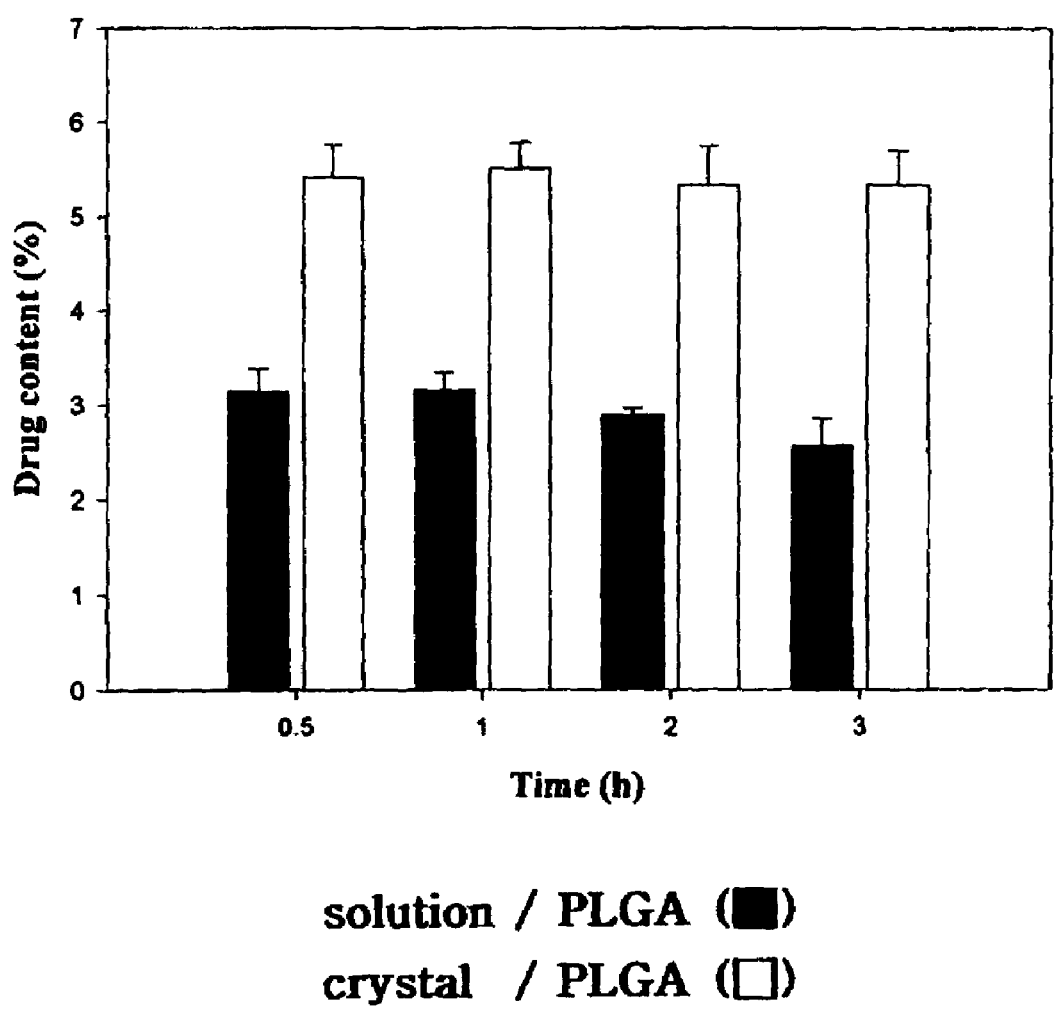
FIG. 6 shows a decrease in the drug content of solution/PLGA and crystal/PLGA in the course of removing $CH_2Cl_2$.
Figure 7:
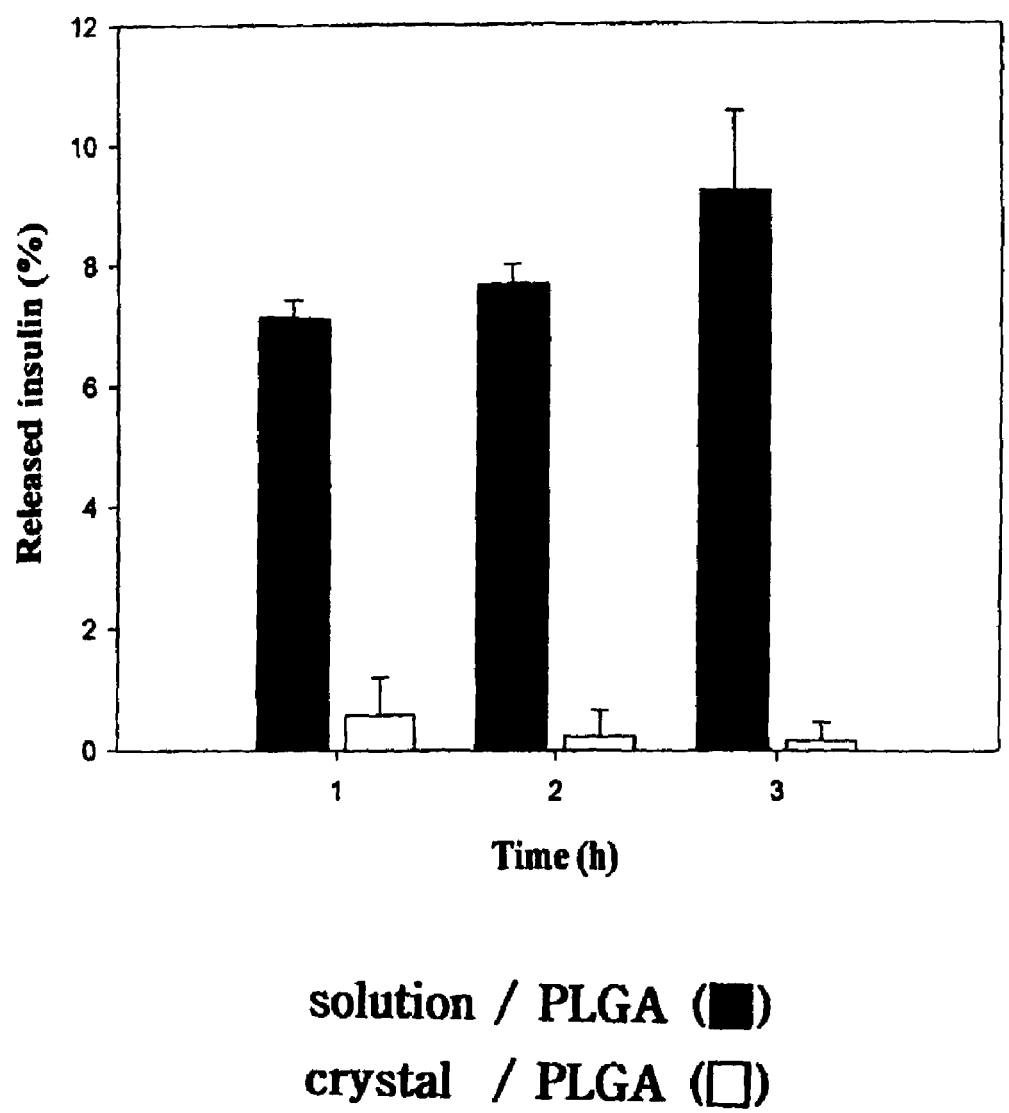
FIG. 7 shows the amounts of released insulin of solution/PLGA and crystal/PLGA in the course of removing $CH_2Cl_2$.

Also, in the case of microencapsulating insulin crystals according to the present invention, the contact surface with an organic solvent is reduced, which suppresses protein denaturation that may occur during the process, thereby greatly increasing the stability of formulation (see FIGS. 6 and 7).

In addition, the crystal/PLGA showed a higher microencapsulation efficiency than the solution/PLGA (see FIG. 8), and loss of protein, which may occur in the course of hardening, was also reduced.

The experimental result of the present inventor showed that insulin was dissolved up to approximately 254 IU/0.3 ml in a 0.1 N acetic solution (pH 2.0). By contrast, since insulin crystals had no limit in solubility, more than approximately 425 IU/0.3 ml of insulin could be induced into microencapsulation. The crystal/PLGA showed a constant encapsulation efficiency of approximately 79% and a linear increase in drug content as the insulin content increased. On the other hand, the solution/PLGA showed the maximum drug content of 3% in view of the solubility of insulin and a decrease in encapsulation efficiency as the insulin content increased. Therefore, it was confirmed that the load of the lung against the clearance process could be lessened by reducing the amount of a polymeric compound administered into a body by increasing the ratio of the drug to a polymer carrier used in the case of microencapsulation using insulin crystals.

Also, the present invention provides a method of preserving a microparticle preparation of insulin in a liquid phase, by which the microparticle preparation is preserved in an isoelectric buffered solution without freeze-drying the microparticle preparation using the isoelectric point of insulin. It was confirmed that approximately 96% of insulin remained in the microparticles even after 15 hours when the microparticle preparation of insulin crystals was preserved in an isoelectric buffered solution of pH 4.5 to 6.5, that is, at an isoelectric precipitation zone of insulin. Since the insulin microparticle preparation in a liquid phase can be directly administered into the body of a patient without the necessity of dispersing the same in a solution for use, administration is facilitated. Also, since there is no protein denaturation that may occur in the course of freeze-drying, initial burst can be considerably reduced when the insulin microparticle preparation are administered into the body.

Figure 11:
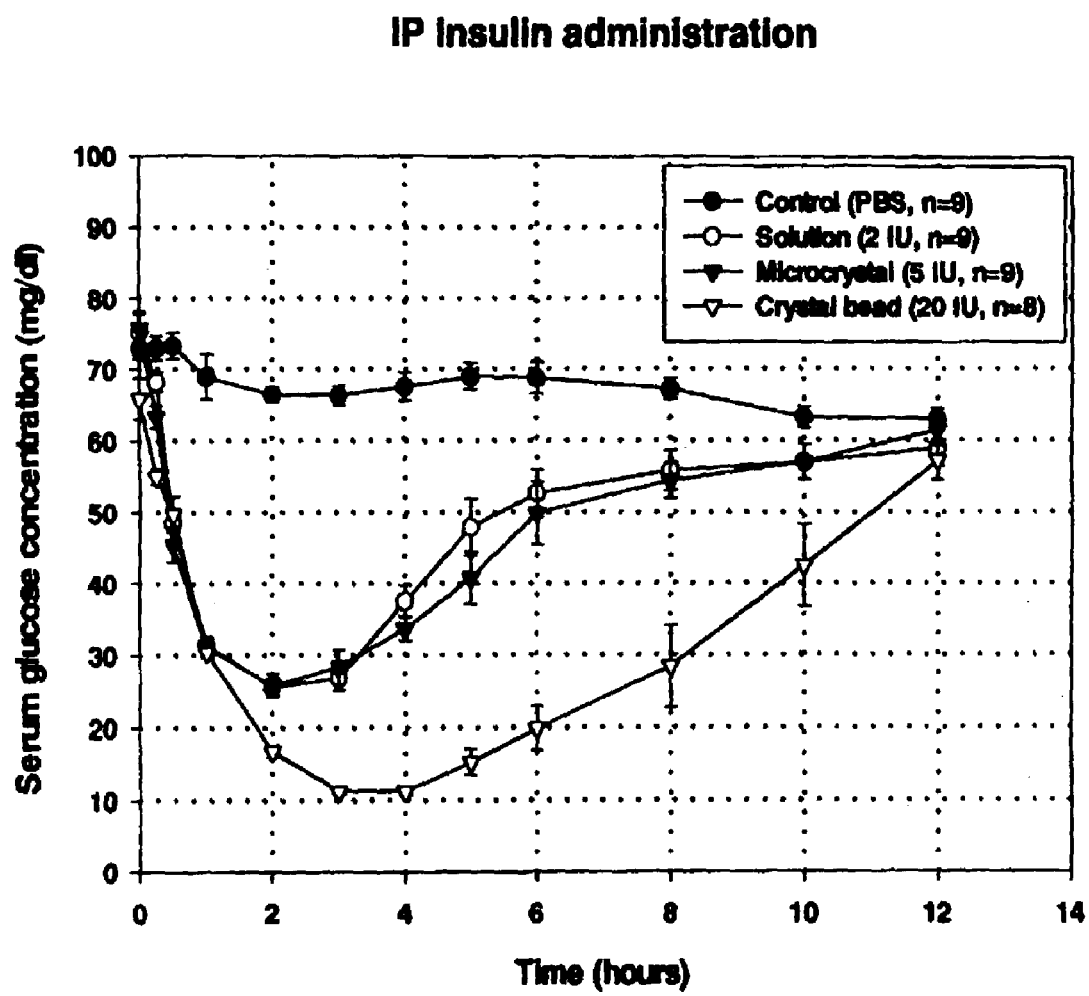
FIG. 11 shows a decrease in serum glucose concentration after administering PBS, insulin solution, insulin crystal and crystal/PLGA into the abdominal cavity of each SD rat.

Animal experiments for verifying exhibition of pharmaceutical efficacy in vivo showed that the crystal/PLGA kept the serum glucose concentration at a lower level for a longer time than non-microencapsulated insulin crystals, while retaining the protracted pharmaceutical efficacy in vivo in more stable manner (see FIG. 11).

The microparticles of the present invention prepared by microencapsulating insulin microcrystals, are used as the controlled release preparation of insulin, by which the pharmaceutical efficacy of insulin can be continuously retained in vivo for a long period of time.

The controlled release preparation of insulin may further include pharmaceutically acceptable diluents, carriers or additives.

Preferably, the controlled release preparation according to the present invention can be made in various forms suitable for pulmonary inhaled administration, injection, oral administration, transdermal suction and so on. The pulmonary inhaled administration form is most preferred.

The controlled release preparation of insulin according to the present invention can be produced using the existing known formulation technique, such that immediate and protracted effects can be simultaneously attained by including an immediately active portion of insulin in the preparation together with microparticles of insulin crystals. Here, usable immediately active portions of insulin may include an insulin solution, existing immediately active insulin preparation and the like.

The present invention will now be described in more detail through various examples. However, the scope of the invention is not limited to these examples, and other and further modification and changes can be made thereto within the true spirit of the invention as set forth in the claims.

EXAMPLE 1

Microencapsulation of insulin crystals (1) Insulin powder was dissolved in an acetate solution of pH 2.0 and the acidity of the resultant was varied using 1 N NaOH and 10 N NaOH. Then, when pH became 4.5, aggregates began to be produced. When the pH was further raised up to 6.0, more than 65% of insulin crystals having a diameter of 5 μm or less were produced. If the pH level of the insulin solution of pH 9.0 to 10.5 was sharply lowered to pH 6, more than 90% of insulin crystals having a diameter of 5 μm or less were produced within several seconds to approximately 2 minutes. In such a manner, the insulin microcrystals existing in a solution phase were prepared.

(2) The prepared solution phase insulin microcrystals were centrifuged at 4,500 rpm for 15 minutes to remove a supernatant solution and insulin microcrystals were separated.

(3) The separated insulin microcrystals were washed with distilled water to remove insulin molecules present in the solution and then suspended in 0.3 ml of the supernatant solution separated in the step (2).

(4) The suspension was poured into 4 ml of a PLGA/$CH_2Cl_2$ solution contained in a glass tube to make an emulsion using a tissue pulverizer.

(5) The emulsion was gradually poured into 50 ml of 1% PVA solution to make a double emulsion.

(6) The double emulsion was stirred for 3 hours to remove $CH_2Cl_2$, centrifuged at 2,300 rpm for 5 minutes to remove a supernatant solution, and then washed three times with distilled water to obtain microparticles according to the present invention, that is, microcapsule-like crystal/PLGA.

EXAMPLE 2 (Comparative example)

Microencapsulation of insulin solution

Microparticles of an insulin solution according to the present invention, that is, microsphere-like solution/PLGA, were prepared in the same manner as in Example 1, except that an insulin solution dissolved in a 0.1 N acetic solution was used instead of insulin microcrystals.

EXAMPLE 3

Measurement of size of insulin microparticles

Figure 2:
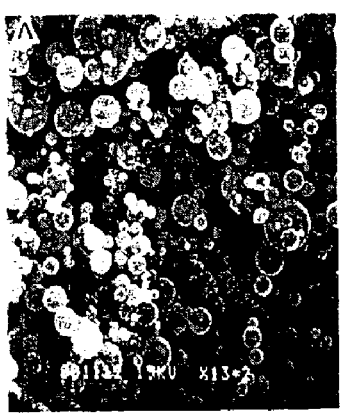
Figure 2:
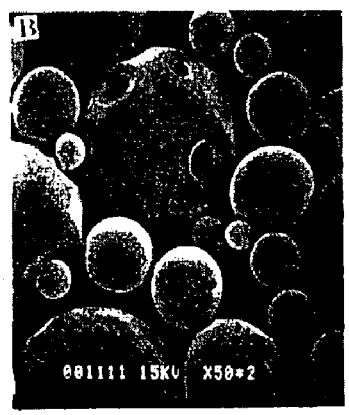
Figure 2:
Figure 2:
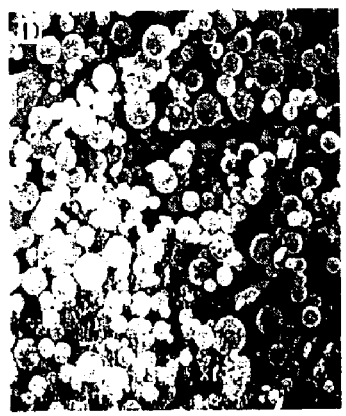
Figure 2:
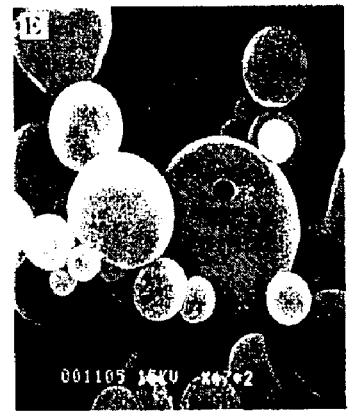
Figure 2:
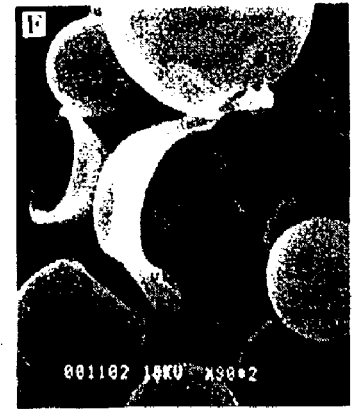
Figure 3:
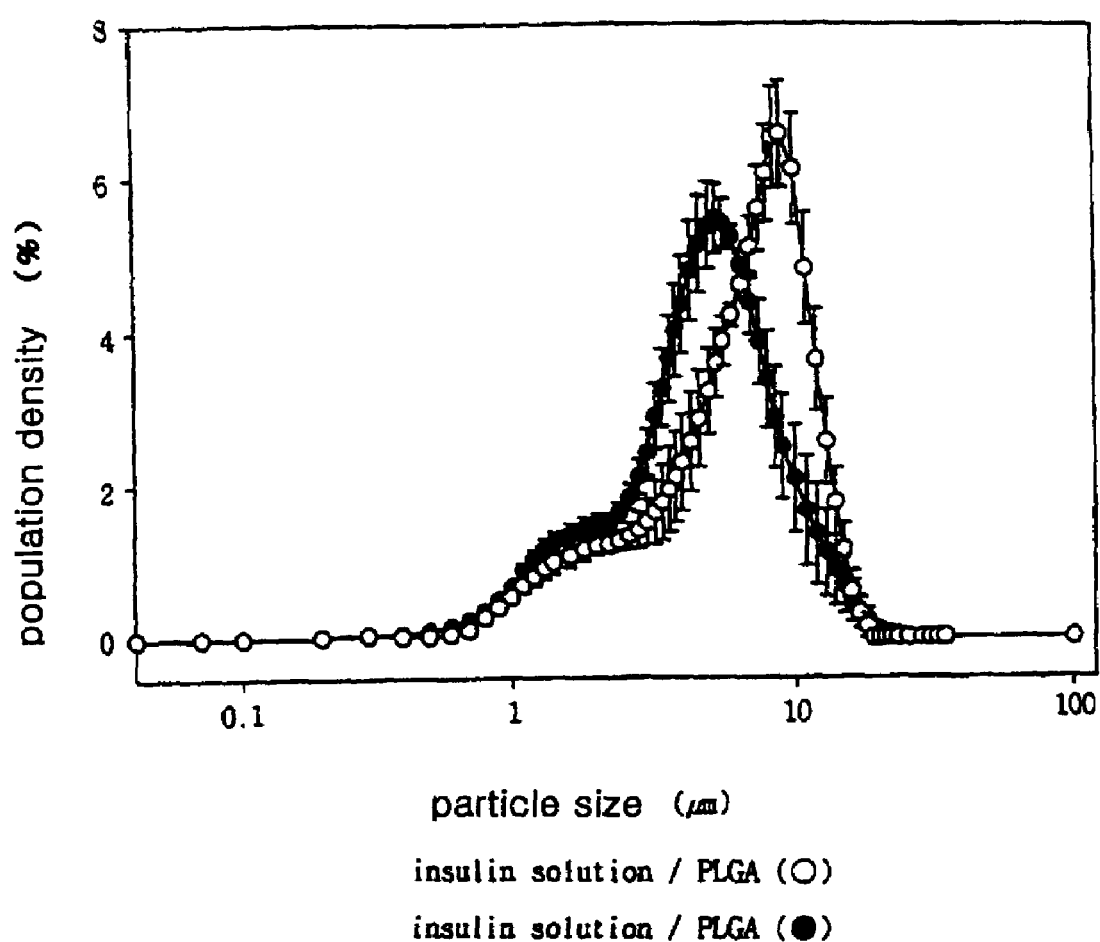
FIG. 3 is a graph showing the result of analyzing particle size of solution/PLGA and crystal/PLGA using a particle size analyzer.
Figure 4:
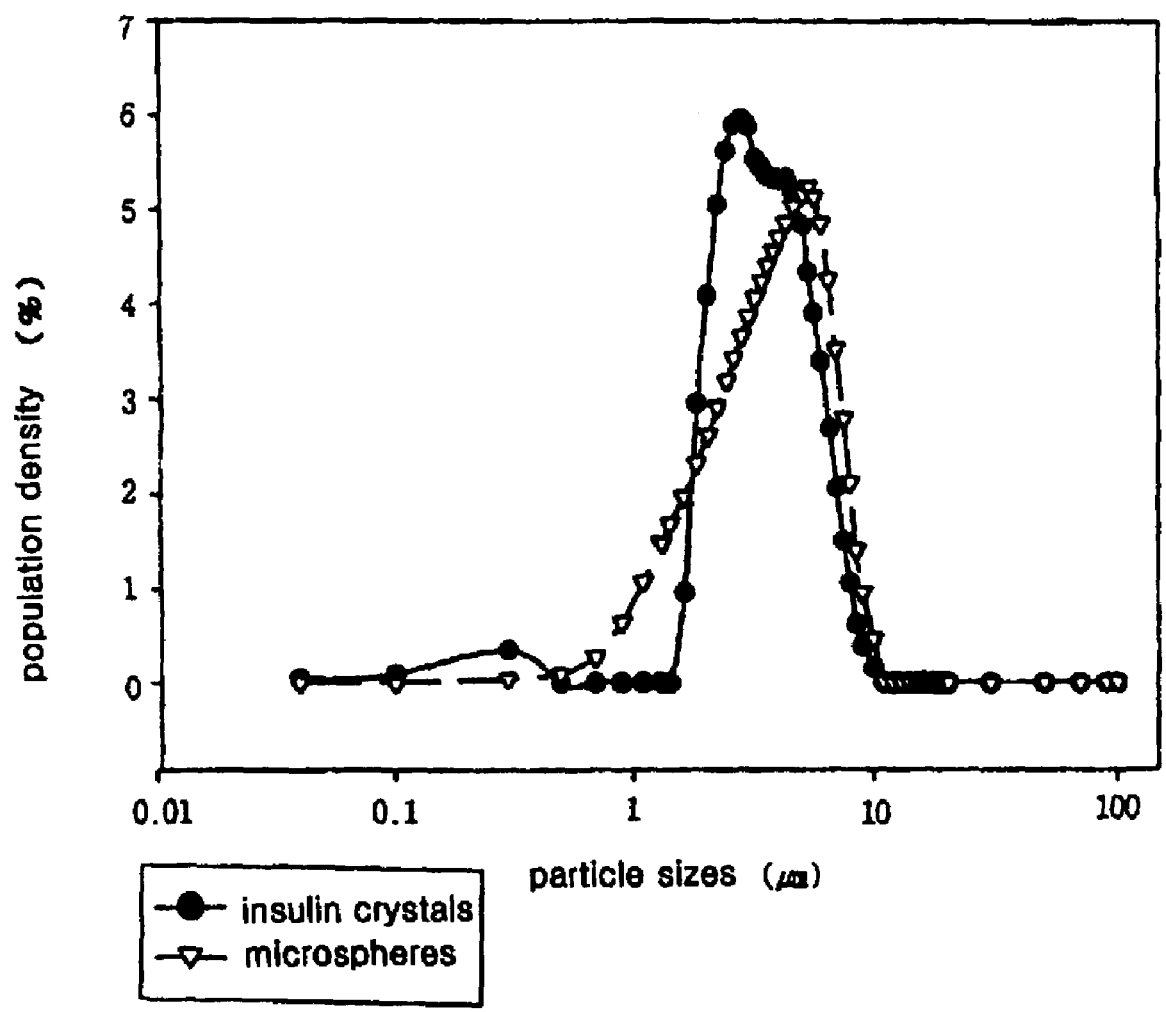
FIG. 4 is a graph showing the result of analyzing a difference in the particle size between insulin crystals and microparticles prepared using the insulin crystals according to the present invention (crystal/PLGA) using a particle size analyzer.
Figure 5A:
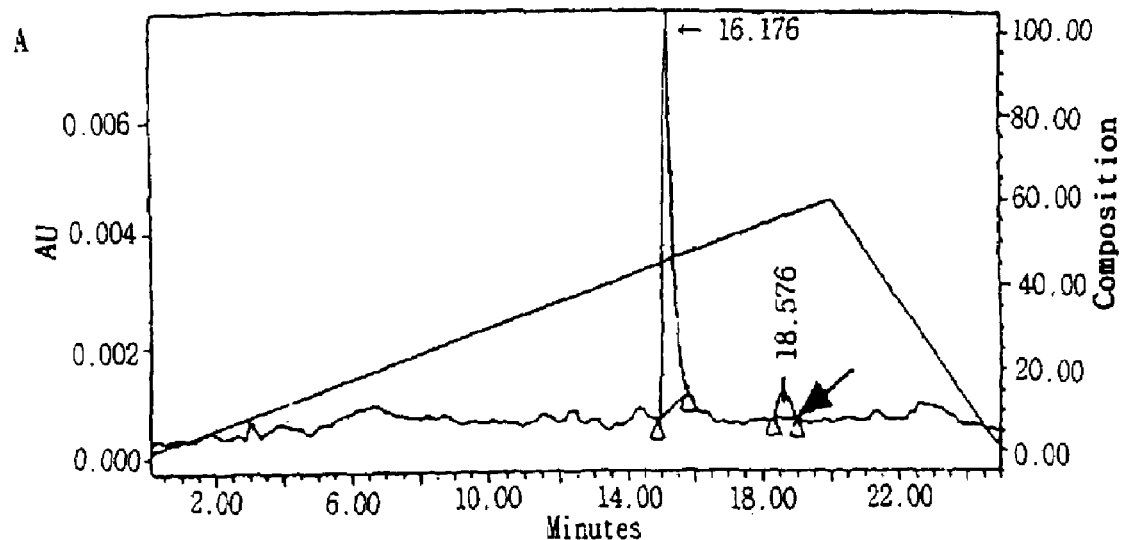
Figure 5B:
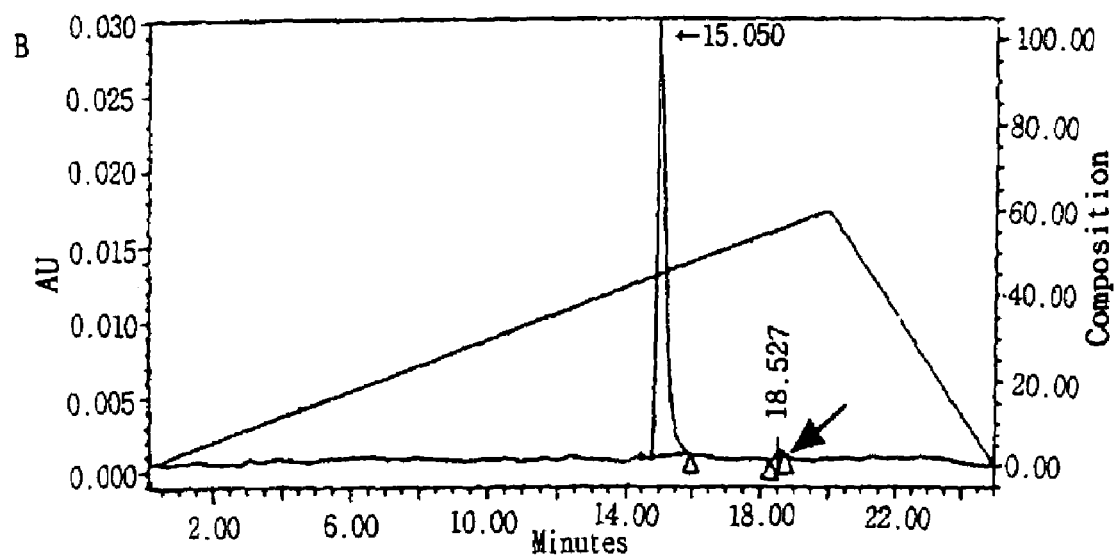
Figure 5C:
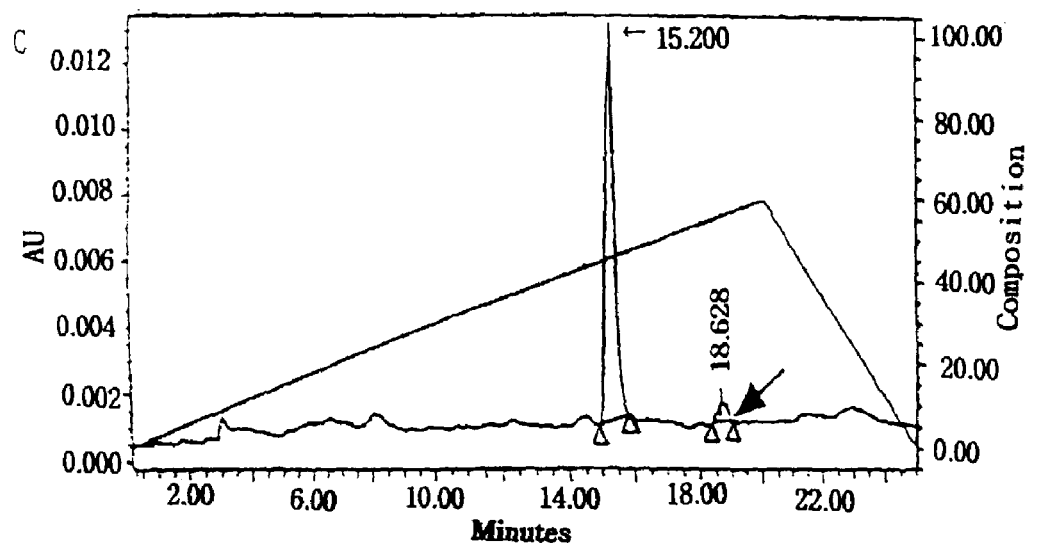
Figure 5D:
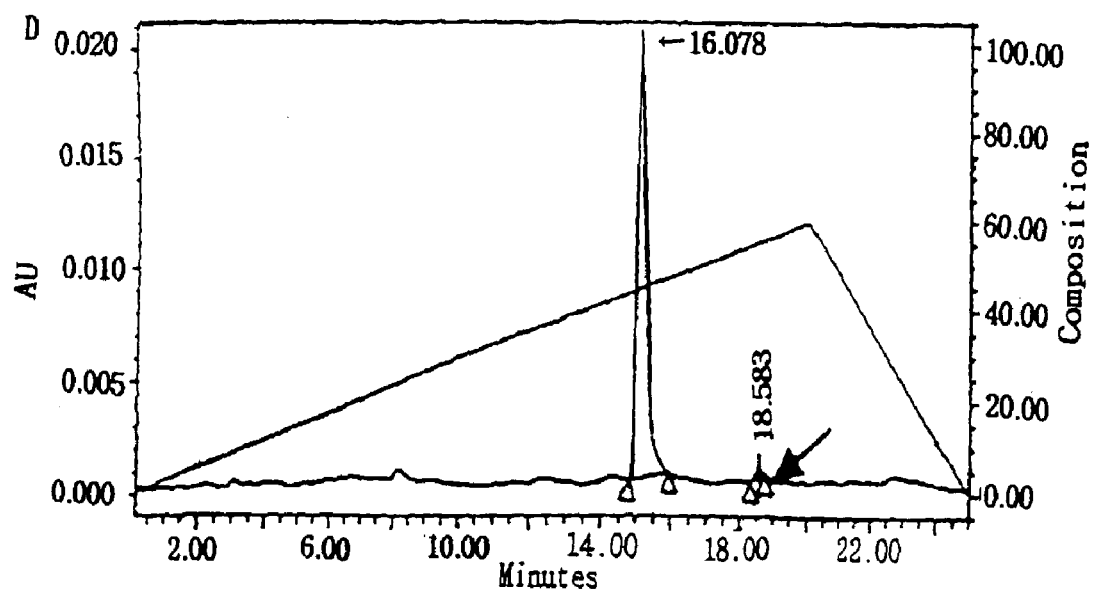

The microparticles prepared in Examples 1 and 2 were observed using an inverted microscope (Model CK2, Olympus, Tokyo, Japan), the observation result being shown in FIG. 1, and the surfaces of the microparticles were observed by scanning electron microscopy (SEM), the observation result being shown in FIG. 2. Also, the size of the microparticles prepared in Examples 1 and 2 were measured, and the measurement result is shown in FIG. 3. The particle size of the insulin crystals prepared in Example 1 (1) and the microparticles (crystal/PLGA) prepared in Example 1 were analyzed, and the analysis result is shown in FIG. 4.

FIGS. 1A and 1C are photographs taken by an inverted microscope, illustrating solution/PLGA prepared in Example 2 (×400 and ×200) and FIGS. 1B and 1D are photographs taken by an inverted microscope, illustrating crystal/PLGA prepared in Example 1 (×400 and ×200). As confirmed in FIG. 1, uniform rectangular microparticles are produced.

Referring to FIG. 2, the crystal/PLGA prepared in Example 1 shows fewer pores on the surface thereof and has the shape of a microcasule having insulin microcrystals therein. On the other hand, the solution/PLGA prepared in Example 2 shows more pores on the surface thereof and has the shape of a microsphere having multi-nuclei therein.

Referring to FIG. 3, the crystal/PLGA prepared in Example 1 has a smaller particle size than the solution/PLGA prepared in Example 2. Referring to FIG. 4 showing the comparison result of insulin crystals and microencapsulated insulin crystals, the particle size of the microencapsulated insulin crystals are slightly greater than those that are not microencapsulated. Although there is a slight difference according to test groups, the microparticles prepared in Example 1 have an average volume diameter of 5.09±0.92 μm, which is large enough for pulmonary delivery. In particular, approximately 60% of the microparticles have a volume-diameter of 5 μm or less, which is a suitable level for administration through the lung, while approximately 99% of the microparticles have a suitable number-diameter.

EXAMPLE 4

Stability test

The crystal/PLGA prepared in Example 1 and the solution/PLGA prepared in Example 2 were dispersed in a PBS solution of pH 7.4 and released at 37° C. After being released for 7 days, the resultant was centrifuged to recover a supernatant solution, and analyzed with RP-HPLC, and the results are shown in FIGS. 5C and 5D.

As confirmed from FIGS. 5A through 5D, deamidated products are observed in both Examples 4 and 5. To get more accurate results, the ratios with respect to the overall insulin peak area are calculated, and cases for non-freeze-dried samples and freeze-dried samples are compared, with the comparison result is shown in Table 1.

TABLE 1

| Sample | | Insulin (%) | Deamidated insulin (%) |
|---|---|---|---|
| Non-freeze-dried | solution/PLGA | 93.17 ± 0.64 | 6.83 ± 0.64 |
| | crystal/PLGA | 98.74 ± 0.20 | 1.26 ± 0.20 |
| Freeze-dried | solution/PLGA | 93.52 ± 3.12 | 6.48 ± 3.12 |
| | crystal/PLGA | 97.80 ± 0.47 | 2.01 ± 0.47 |

As shown in Table 1, the crystal/PLGA prepared in Example 1 had a much smaller amount of deamindation than the solution/PLGA prepared in Example 2, which is smaller than the 3% specified by the British or U.S. pharmacopoeia.

Therefore, the stability of microencapsulated insulin crystal is significantly superior to that of microencapsulated insulin solution, and the stability is maintained even after freeze-drying the samples.

EXAMPLE 6

Processing loss of insulin

In the course of producing the microparticles in Examples 1 and 2, in the step of removing $CH_2Cl_2$, samples were taken at constant time intervals and separated into microparticles and OWP. The microparticles were dissolved in $CH_2Cl_2$ solution and a 0.1 N acetate solution was added thereto to then extract insulin entrapped inside. The pH level of the OWP was lowered to 2 to dissolve insulin microcrystals possibly remaining inside. These were all measured by a Bradford assay and the results thereof are shown FIGS. 6 and 7.

The solution/PLGA exhibits a decrease in drug content while the crystal/PLGA exhibited no decrease in drug content (FIG. 6).

The solution/PLGA exhibits a continuous increase in the amount of insulin released to OWP and, after 3 hours, approximately 9% of the insulin added to the overall system is released outside (FIG. 7).

Therefore, it can be understood that the processing loss of microencapsulated insulin crystal is noticeably smaller than that of microencapsulated insulin solution.

EXAMPLE 7

Drug content in microparticle and encapsulation efficiency

Figure 8:
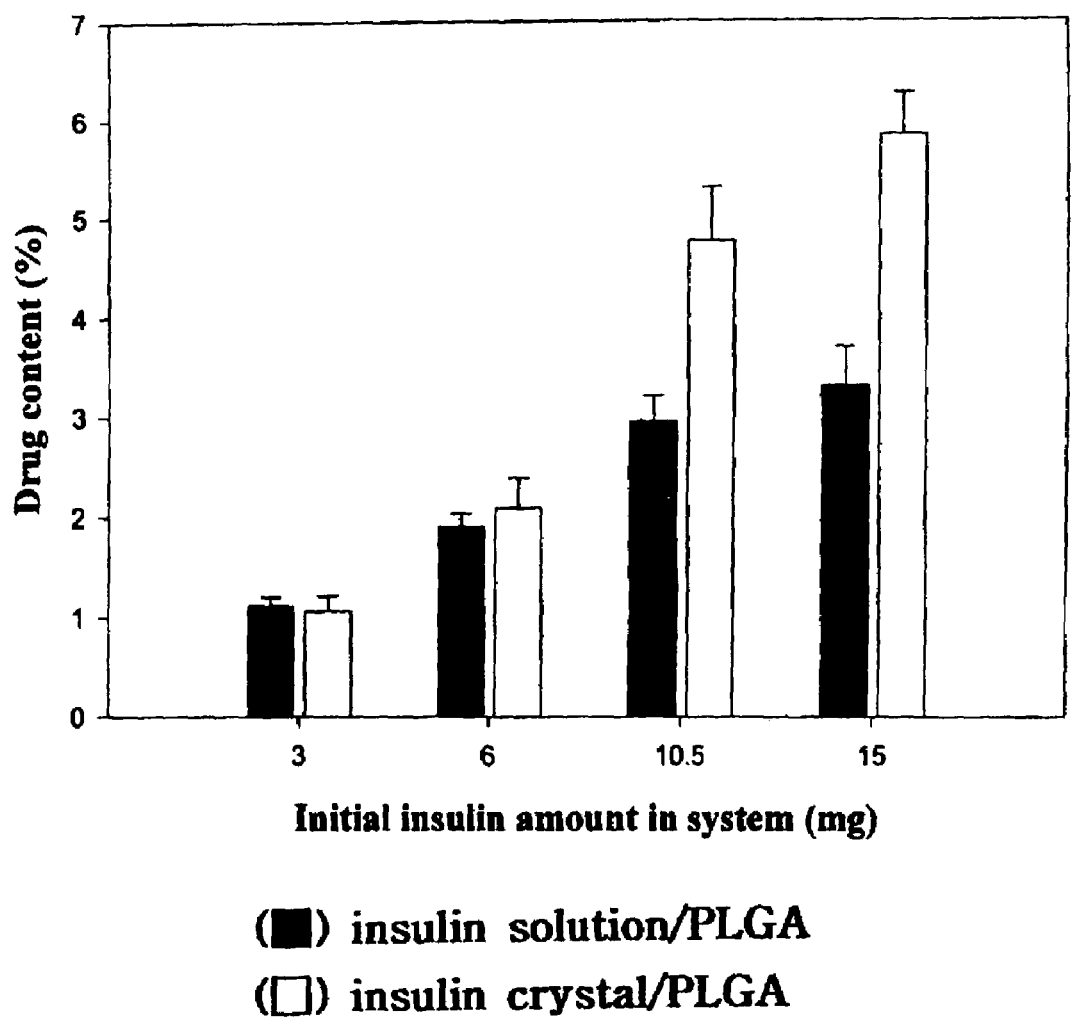
FIG. 8 shows the relationship between drug content and initial insulin amount used in of solution/PLGA and crystal/PLGA.

Predetermined amounts of insulin suspension prepared in the same manner as in Example 1(1) were taken to give 3 mg, 6 mg, 10.5 mg and 15 mg of insulin crystals. The samples were centrifuged and dispersed in 0.3 ml of crystal soup with the supernatant thrown away. Then, microparticles were produced in the same manner as in Example 2. The resultants were freeze-dried and approximately 5 mg of each sample was taken and then insulin contained therein was extracted in the same manner as in Example 6 to measure the drug content and encapsulation efficiency. The results are shown in FIG. 8 and Table 2.

TABLE 2

Encapsulation efficiencies of solution/PLGA and crystal/PLGA

| Insulin content (mg) | | Encapsulation efficiency (%) | S.D | S.E |
|---|---|---|---|---|
| solution/PLGA | 3 | 72.91 | 7.98 | 4.61 |
| | 6 | 63.10 | 6.52 | 3.76 |
| | 10.5 | 52.72 | 6.77 | 3.91 |
| | 15 | 42.75 | 6.90 | 3.98 |
| crystal/PLGA | 3 | 73.99 | 18.85 | 10.88 |
| | 6 | 69.66 | 18.18 | 10.50 |
| | 10.5 | 80.47 | 13.24 | 7.64 |
| | 15 | 79.85 | 7.96 | 4.59 |

(S.D: Standard deviation; S.E: Standard error)

The above table 2 demonstrates mean values of data of three-times test results.

The crystal/PLGA showed a constant encapsulation efficiency of approximately 79% and a linear increase in drug content as the insulin content increased. On the other hand, the solution/PLGA showed the maximum drug content of 3% in view of the solubility of insulin and a decrease in encapsulation efficiency as the insulin content increased. Therefore, it was confirmed that in the case of microencapsulating insulin microcrystals, the drug content in the microparticle increased compared to the conventional method in which the insulin solution is capsulated, and the processing loss was also reduced, resulting in an increase in the encapsulation efficiency.

EXAMPLE 8

Release test

In order to evaluate the effect of microencapsulation related to release of insulin, insulin crystals were microencapsulated and some were freeze-dried while the other were non-freeze-dried. Then, the release test was carried out with the insulin crystals. Insulin crystals (●), freeze-dried microcapsules prepared in Example 1 (○) and non-freeze-dried microcapsule prepared in Example 1 (▲) were mixed with 0.4 ml of a PBS solution of pH 7.4 to then be released 37° C. Centrifuging was performed at constant time intervals, the supernatant solution was recovered and a new solution was replenished. The amounts of released insulin were measured by a Bradford assay method, and the result thereof is shown in FIG. 9.

Figure 9:
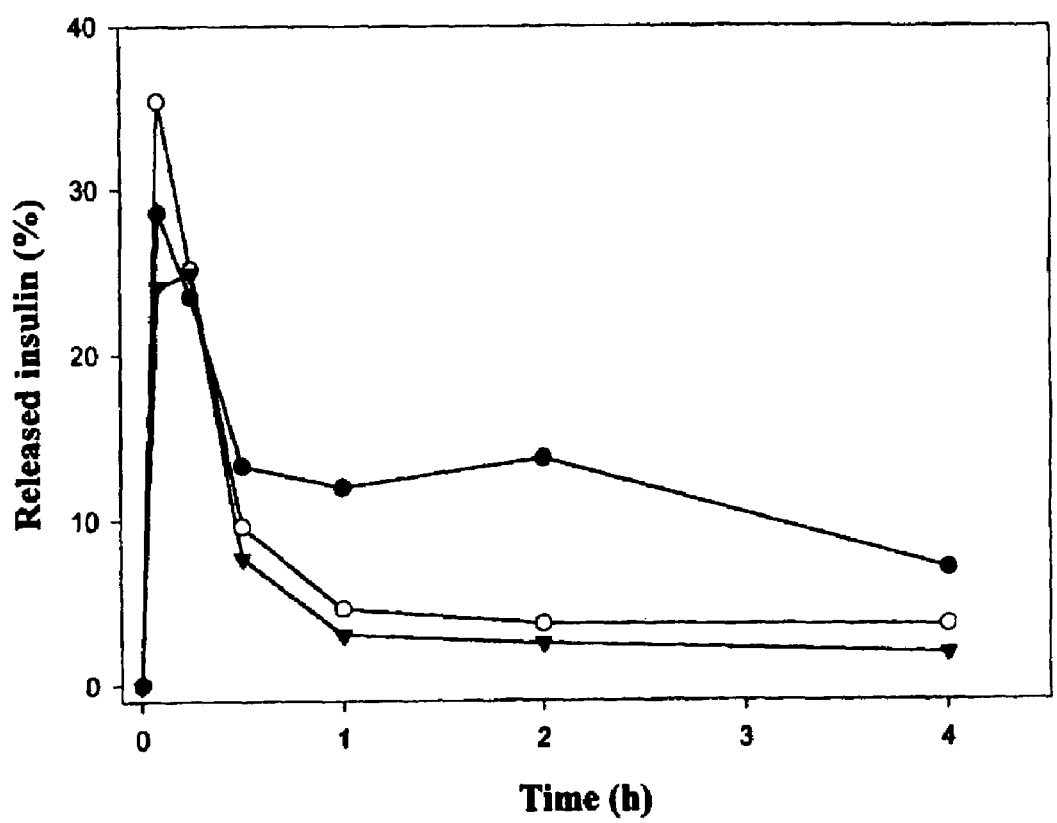
FIG. 9 is a graph showing a change of released insulin crystal, microencapsulated insulin crystal and microencapsulated freeze-dried insulin crystal over time.

As shown in FIG. 9, the insulin showed a biphasic release phenomenon, that is, an initial burst phase and a zero-order release phase. While the release amount of insulin crystals was approximately 28%, the release amount of microcapsulated and freeze-dried insulin crystals (crystal/PLGA) was 36%, that is, an increase of approximately 8%. Conversely, while the initial burst of the non-freeze-dried microparticles (crystal/PLGA) was approximately 24%, that is, a decrease of approximately 4% compared to the insulin crystals, and a decrease of approximately 12% compared to the freeze-dried microparticles. Conclusively, the release amount is presumably controlled by a polymeric layer.

In the case of the insulin microcrystals, a large amount of released insulin microcrystals was continuously released until they were completely released after 4 hours, with no insulin microcrystals remaining. However, in the case of the microcapsulated insulin crystals, a large amount of insulin was released at an initial stage and then a smaller amount of insulin was continuously released. Even after 4 hours since the insulin released first, 38% of the non-freeze-dried insulin microcrystals and 18% of the freeze-dried insulin microcrystals remained in the microparticles.

As a result, it was confirmed that non-freeze drying and microencapsulation could considerably reduce initial burst of insulin. In particular, in the case of non-freeze drying and microencapsulation, a uniform amount of insulin was continuously released for a long time compared to the case of insulin crystals.

EXAMPLE 9

Preservation test using isoelectric point

Figure 10:
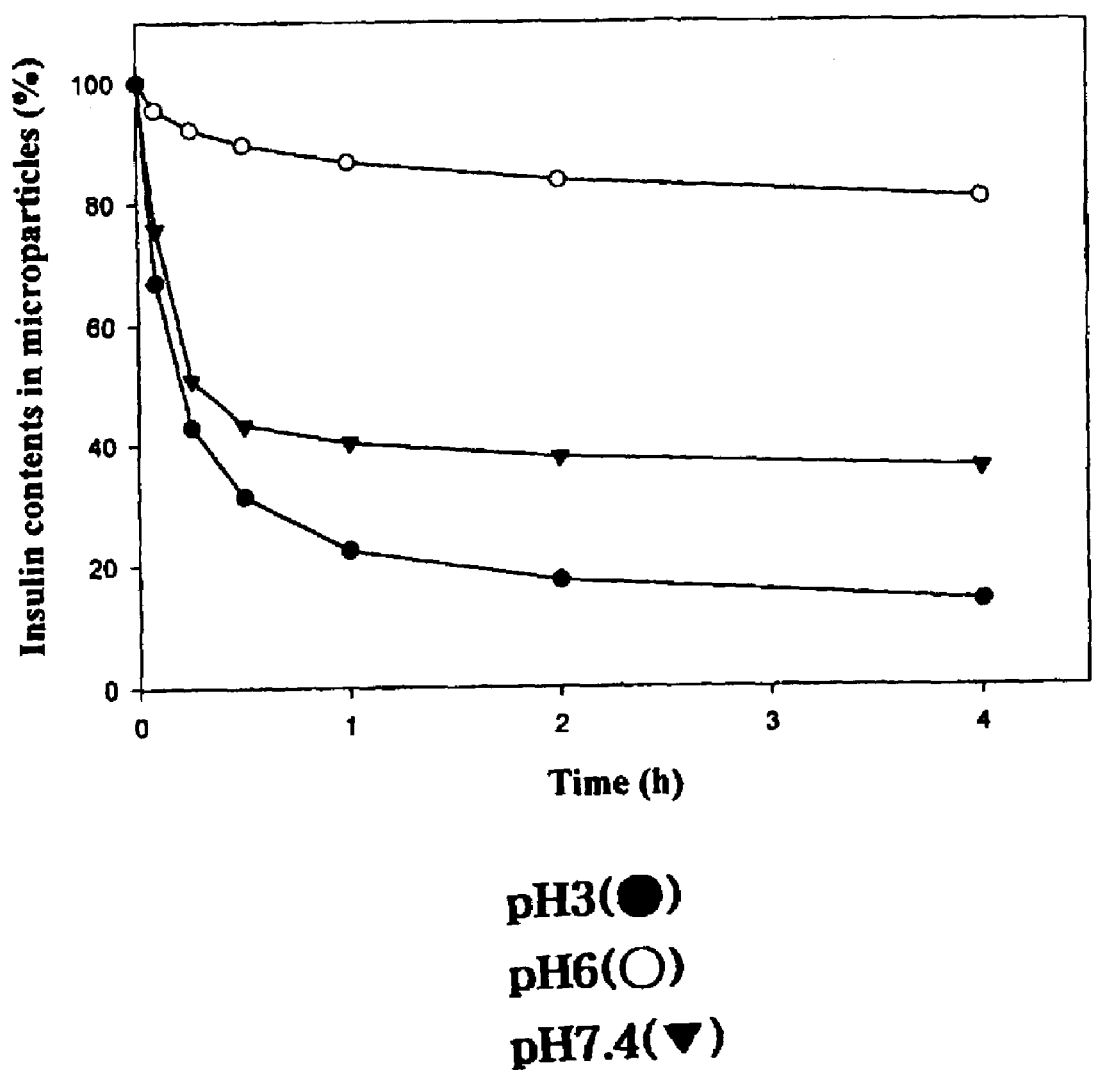
FIG. 10 shows insulin contents remaining in microparticles of non-freeze-dried crystal/PLGA in PBS solutions of pH 3, pH 6 and pH 7.4, respectively.

In a state in which the microcapsules prepared in Example 1 were not freeze-dried, release tests were carried out in the same manner as in Example 8 in PBS solutions of pH 3 (●), at which insulin is completely dissolved, pH 6 (○), that is, an isoelectric precipitation zone of insulin, and pH 7.4 (▼), respectively, and the results thereof are shown in FIG. 10.

The test results showed that approximately 20% of overall insulin was released in the solution of pH 6 (○) after 4 hours, that is, 80% of insulin remained, and 15% and 38% of insulin remained in solutions of pH 3 (●) and pH 7.4 (▲), respectively. As a result, a small amount of insulin was released slowly at pH 6, unlike at pH 3 and pH 7.4.

Also, when the sample was preserved in the PBS solution of pH 6 at 4° C., 96% of insulin remained in the microparticles even after 15 hours.

EXAMPLE 10

Preliminary clinical trials based on insulin formulations

An insulin solution prepared by dissolving insulin in a PBS solution of pH 7.2, insulin microcrystals used in Example 1 and microcapsules prepared in Example 1 were abdominally injected into the SD rats. The insulin solution was completely dissolved in a PBS solution of pH 2.14 and then its pH level was adjusted to 7.2 using NaOH and HCl. The optimal doses for the respective preparations were selected and then administered to the rats. In the case of the insulin solution, 2 IU/kg of the insulin solution was administered into the abdominal cavities of 9 SD rats. In the case of insulin microcrystals having an average particle size of 4.16 μm and a yield of 94.25%, 5 IU/kg of insulin microcrystals were administered into the abdominal cavities of 9 SD rats. 20 IU/kg of microencapsulated insulin microcrystals were administered into abdominal cavities of 8 SD rats. By comparison, a PBS solution of pH 7.2 was administered into a control group of 9 SD rats. The dosage for each rat was the same as in the insulin suspension according to the weight of each rat. The results thereof are shown in FIG. 11.

It was confirmed that noticeable decreases in serum glucose concentration were observed in the insulin-injected rats (○, ▼, ▽) compared to the control group (●). In the case of the insulin solution (○), its pharmaceutical effect lasted only 6 hours or so. In the case of the insulin crystals (▼), its pharmaceutical effect lasted approximately 8 hours. In the case of the crystal/PLGA (▽), its pharmaceutical effect lasted approximately 12 hours.

Also, it was confirmed that microcapsulated crystal/PLGA (▽) retained a lower serum glucose concentration for a longer period of time than the insulin crystals (▲).

In other words, the insulin solution (○) showed a minimum level in serum glucose concentration at a time of 2 hours elapsed, and the same is applicable to the insulin crystals (▲). The insulin microcapsule (▽) showed a minimum level in serum glucose concentration at a time of 3 hours elapsed. Since the release pattern of insulin can be deduced from the pattern of serum glucose concentration, the maximum amount of released insulin can be identified when the serum glucose concentration is at the lowest level.

After the lowest levels in the serum glucose concentrations were shown in the cases of the insulin solution (○) and the insulin crystals (▲) at a time of 2 hours elapsed, the serum glucose levels were recovered to normal levels after 6 to 8 hours. On the other hand, the serum glucose level of the insulin microcapsule (▽) was not recovered to the normal level until 12 hours was elapsed on the basis of the time of 3 hours elapsed. This means that microcapsules release insulin slowly in a body, thereby increasing the pharceutical effect lasting time.

If greater than 5 IU/kg of the insulin solution is administered, or if 10 IU/kg of insulin microcrystals is administered, the rats died due to hypoglycemia. However, in the case of the insulin microcapsule (▽), even if it was administered at a dose of 20 IU/kg, the serum glucose level was dropped and then slowly recovered to the normal level. This means that drug is slowly released in vivo by polymeric materials to protract the exhibition time of pharmaceutical efficacy, thereby effectively preventing diabetes patients from dying due to shock or death presumably caused by hypoglycemia.

Table 3 shows the dose, the minimum reduction of plasma glucose (MRPG), the time of minimum serum glucose concentration, the area under the serum glucose concentration-time curve (AUC), and the total reduction of plasma glucose (TRPG). That is to say, the behavior of insulin in vivo can be understood from Table 3.

TABLE 3

|  | Dose (IU/kg) | MRPG (ml/dl) | Time (h) of minimum serum glucose concentration | AUC (mg h/dl) | % TRPG |
|---|---|---|---|---|---|
| Control group | 0 | 63 ± 1.39 | 12 | 803.01 | 8.74 |
| Insulin solution | 2 | 25.56 ± 1.24 | 2 | 582.9 | 35.52 |
| Insulin crystal | 5 | 25.78 ± 1.56 | 2 | 553.47 | 39.22 |
| crystal/PLGA | 20 | 11.25 ± 0.41 | 3 | 346.75 | 56.14 |

AUC: Area under the serum glucose concentration-time curve
MRPG: Minimum reduction of plasma glucose
TRPG: Total reduction of plasma glucose
% TRPG: 100 × [1 − (AUC/Time × maximum point)]

Industrial applicability

As confirmed from the above-described examples, the controlled release preparations of insulin according to the present invention, in which insulin microcrystals are microencapsulated, can reduce denaturation of insulin, occurring during microencapsulation and can increase the stability of preparations, thereby reducing initial burst of insulin in a living body and preventing the risk of hypoglycemia. Also, according to the present invention, small, uniform sized microparticles are obtained, which is suitable for pulmonary delivery. Further, an encapsulation efficiency, that is, a ratio of drug to a polymer carrier, is increased, which is suitable for administration through the lung or injection. Since the controlled release preparation of insulin according to the present invention exhibits stable pharmaceutical efficacy in a living body continuously for a long period of time, it is possible to adjust the serum glucose concentration of a diabetes patient in a more stable manner while reducing the number of administrations.

What is claimed is:

1. A controlled release preparation of insulin containing microparticles having a volume average diameter of 10 μm or less obtained by microencapsulation of insulin microcrystals having a volume average diameter which is less than the volume average diameter of the microparticles,
   wherein the insulin microcrystals are formed by varying the pH of an acidic insulin solution, which is at an isoelectric point or below, up to within the range 9 to 10.5 to form insulin seeds that can act as nuclei of crystal; and lowering the solubility of insulin in the solution by lowering the pH of the solution,
   wherein the microencapsulation is performed by double emulsion method comprising suspending the insulin microcrystals in a solution of pH 4.5 to 6.5, which is. an isoelectric precipitation zone; adding the suspended solution to a biodegradable polymer solution to make a primary emulsion; adding an emulsifier to the primary emulsion to make a secondary emulsion; and stirring the secondary emulsion to form microparticles.

2. The controlled release preparation of insulin containing microparticles according to claim 1, wherein the microparticles are preserved in an isoelectric buffered solution of pH 4.5 to 6.5.

3. The controlled release preparation of insulin containing microparticles according to claim 1 or 2, wherein the biodegradable polymer is selected from the group consisting of albumin, gelatin, collagen, fibrinogen, polylactides(PLA), polyglycolides (PGA), poly (lactide-co-glycolide)s (PLGA), polyethylene glycol (PEG), poly β-hydroxy butyric acid (PHB), polycaprolactone, polyanhydrides, polyorthoesters, polyurethanes, poly(butyric acid)s, poly(valeric acid)s, poly (lactide-co-caprolactone) and derivatives thereof, and copolymers thereof.

4. The controlled release preparation of insulin containing microparticles according to claim 3, wherein the polymer is a poly(lactide-co-glycolide)s (PLGA).

5. The controlled release preparation of insulin containing microparticles according to claim 1 or 2, wherein the solution for suspending the insulin crystals is one selected from the group consisting of a chitosan solution produced from a 1% acetate solution, a phosphate buffered saline (PBS) solution and supernatant solution obtained after centrifugation of insulin microcrystal solution.

6. The controlled release preparation of insulin containing microparticales according to claim 1 or 2, wherein the preparation has one of formations for pulmonary inhaled administration, injection, oral administration and transdermal suction.

7. The controlled release preparation of insulin containing microparticles according to claim 1 or 2, further comprising pharmaceutically acceptable diluents, carriers and additives.

8. The controlled release preparation of insulin containing microparticles according to claim 1 or 2, wherein an immediately active insulin is also included.

9. A method of producing a controlled release preparation comprising the steps of:
(a) varying the pH of an acidic insulin solution, which is at an isoelectric point or below, up to within the range 9 to 10.5 to form insulin seeds that can act as nuclei of crystal; and lowering the solubility of insulin in the solution by lowering the pH of the solution to form insulin microcrystals,
(b) suspending the insulin microcrystals in a solution of pH 4.5 to 6.5, which is an isoelectric precipitation zone; adding the suspended solution to a biodegradable polymer solution to make a primary emulsion; adding an emulsifier to the primary emulsion to make a secondary emulsion; and stirring the secondary emulsion to form microparticles having a volume average diameter of 10 μm or less and greater than a volume average diameter of the microcrystals,
(c) preparing formulation by a general pharmaceutical method by adding pharmaceutically acceptable supportive ingredients or additives to the microparticles.

10. The method according to claim 9, wherein the step (c) includes the step of preserving the microparticles in an isoelectric buffered solution of pH 4.5 to 6.5.

11. The method according to claim 9 or 10, wherein the emulsifier is one of polyvinylaichol (PVA), polyvinylpirrolidone, alginates, methylcellulose and gelatine.

12. The method according to claim 9 or 10, wherein the solution for suspending the insulin crystals is one selected from the group consisting of a chitosan solution produced from a 1% acetate solution, a phosphate buffered saline (PBS) solution and asupematant solution obtained after centrifugation of insulin microcrystal solution.

* * * * *